United States Patent [19]

Marets

[11] 4,268,480
[45] May 19, 1981

[54] DEVICE FOR MEASURING A PHYSICAL OPERATING CHARACTERISTIC OF AN OZONIZER

[75] Inventor: Maurice Marets, Sevran, France

[73] Assignee: Trailigaz, Compagnie Generale de l'Ozone, Garges les Gonesse, France

[21] Appl. No.: 40,824

[22] Filed: May 21, 1979

[30] Foreign Application Priority Data

May 23, 1978 [FR] France .................. 78 15259

[51] Int. Cl.³ .................. B01D 11/00; B01F 1/00
[52] U.S. Cl. .................. 422/98; 23/232 E; 73/23; 324/78 J; 324/78 E; 324/71 R; 324/464; 204/176
[58] Field of Search .................. 23/232 R, 232 E; 422/98; 73/23; 324/78 E, 78 J, 7 R, 464; 204/176

[56] References Cited

U.S. PATENT DOCUMENTS

| 3,528,779 | 9/1970 | Fontijn | 23/232 E |
| 3,569,825 | 3/1971 | Lilienfeld | 324/464 |
| 3,881,869 | 5/1975 | Neti et al. | 23/232 R |
| 3,975,159 | 8/1976 | Van Heusden | 23/232 E |

FOREIGN PATENT DOCUMENTS 573765 10/1977 U.S.S.R. .................. 324/78 J

OTHER PUBLICATIONS

*Fundamentals of Electronics,* vol. 4, Bureau of Naval Personnel, Wash., D.C., 1964, pp. 164-166.

Primary Examiner—William F. Smith
Assistant Examiner—Chris Konkol
Attorney, Agent, or Firm—Sughrue, Rothwell, Mion, Zinn and Macpeak

[57] ABSTRACT

This device for measuring a physical operating characteristic of an ozonizer such as, for example, the ozonization power, the production of ozone or the concentration of ozone in the air, comprises a medium or high-frequency sensor placed in the ozonization zone of the ozonizer and an electronic processing circuit which delivers a signal which is an image of the energy received by the sensor. The sensor detects the medium or high-frequency energy produced in the ozonizer and produces a signal which is an image of one of the aforementioned physical characteristics owing to the fact that the curves of these characteristics are colinear with those of the medium and high-frequency energy components.

8 Claims, 3 Drawing Figures

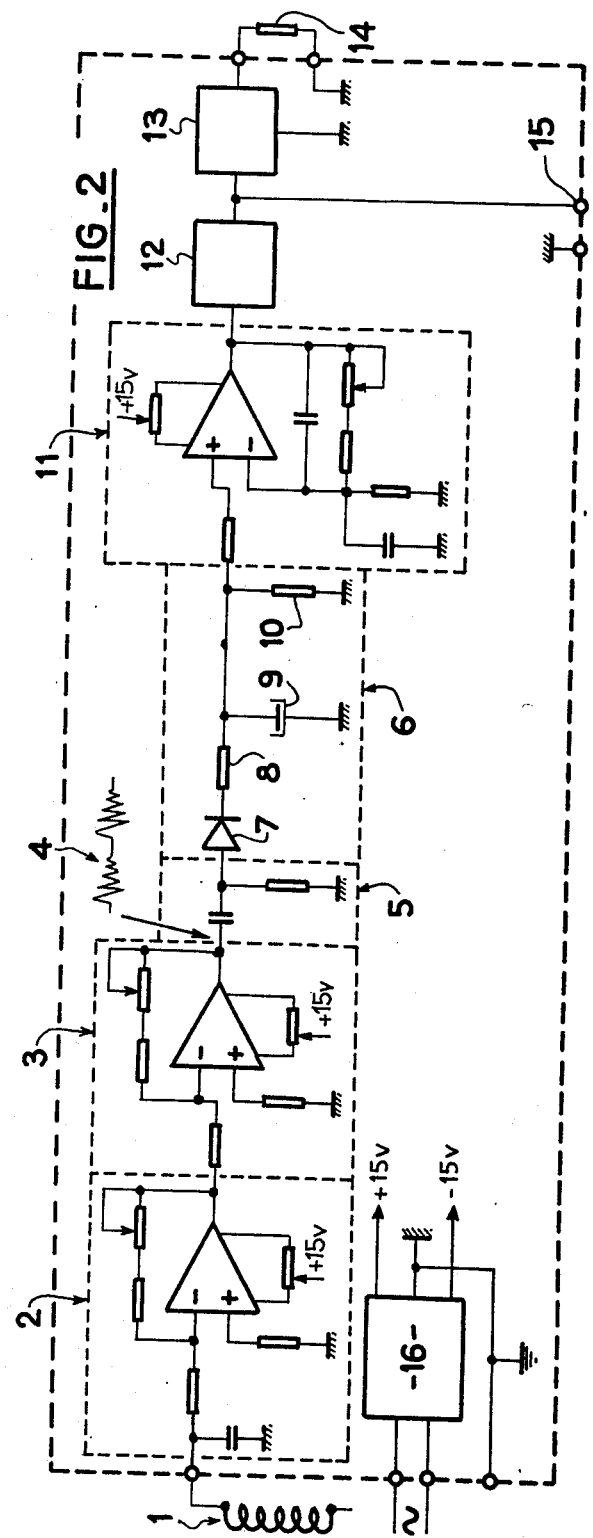

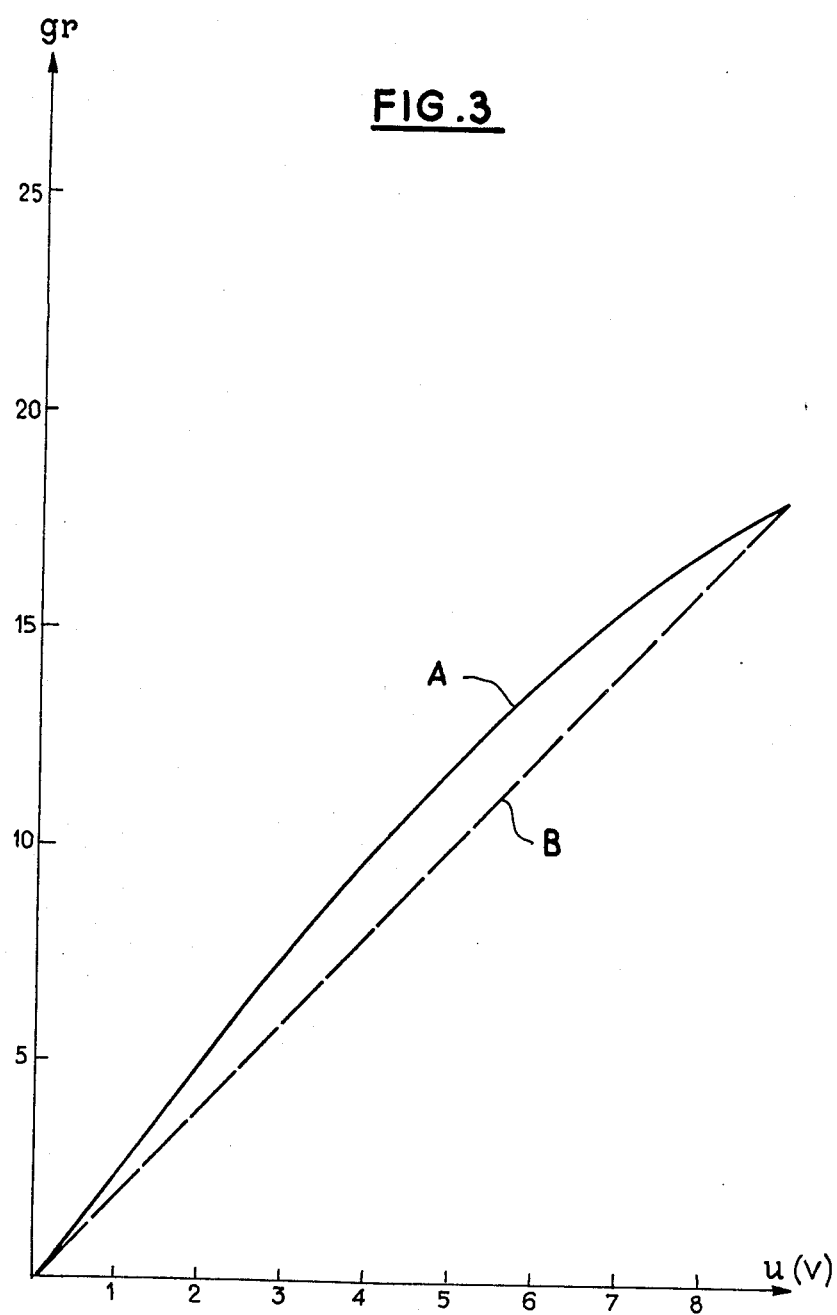

DEVICE FOR MEASURING A PHYSICAL OPERATING CHARACTERISTIC OF AN OZONIZER

DESCRIPTION

The present invention relates to the production of ozone and to apparatus termed ozonizers and more particularly concerns a process and a device for measuring a physical operating characteristic of an ozonizer such as for example the ozonization power, the production of ozone or the concentration of ozone in the air.

An ozonizer of conventional construction comprises a series of discharge elements each of which is formed by two coaxial cylindrical electrodes which are separated by a dielectric and between which a stream of air or other gas containing oxygen circulates. This series of elements is supplied with power in parallel by the secondary winding of a step-up transformer the primary winding of which is connected to the mains by a control device, for example having thyristors, whereby it is possible to vary the supply power within a range of from 5 to 100% of the maximum power.

In certain circumstances, it is desirable to measure a physical operating characteristic of the ozonizer such as, for example, the ozonization power, the production of ozone or the concentration of ozone in the air. It may in particular be desirable to measure such a characteristic if it is desired to construct a servo-system in which the output magnitude would be a physical or chemical magnitude which is a function of the production of ozone or of the electric power supplied to the ozonizer. The signal delivered by the measuring device would then be a magnitude which anticipates the function related to the ozonizing power.

For this purpose, the power supply to the ozonizer from the sinusoidal voltage of the mains chopped by the action of the thyristors may be for example measured. However, such a measurement is delicate and the means for achieving it are expensive.

Consequently, an object of the invention is to provide a process and a device for measuring a physical operating characteristic of an ozonizer which is simple and cheap.

According to the invention, there is provided a process for measuring a physical operating characteristic of an ozonizer, such as, for example, the ozonization power, the production of ozone or the concentration of ozone in the air, wherein the medium or high frequency signal emitted by the ozonizer is detected and an electric signal is produced which is an image of the detected medium or high frequency signal.

The invention also provides a device for carrying out said process which comprises a medium or high-frequency sensor placed in the vicinity of the ozonizer and an electronic processing circuit which delivers said signal which is an image of the energy received by the sensor.

According to one feature of the invention, said sensor is an antenna.

According to another feature of the invention, the sensor is a dividing bridge.

According to yet another feature of the invention, the electronic circuit comprises an integrator circuit or diode pump, comprising a capacitor, a diode charging the capacitor, and a resistor discharging the capacitor, the integrator circuit having distinct charging and discharging time constants and being so arranged that, when balanced, the voltage at the terminals of the capacitor is the image of the signal received by the sensor.

Further features and advantages of the invention will be apparent from the ensuing description with reference to the accompanying drawings which are given solely by way of example and in which:

FIG. 2 is a diagram showing the sensor and the electronic processing circuit according to the invention, and FIG. 3 is a graph showing the real curve of the production of ozone as a function of the output voltage of the integrator circuit and the curve, rendered linear, of the production of ozone as a function of the voltage at the output of the multi-function generator.

Figure 1:
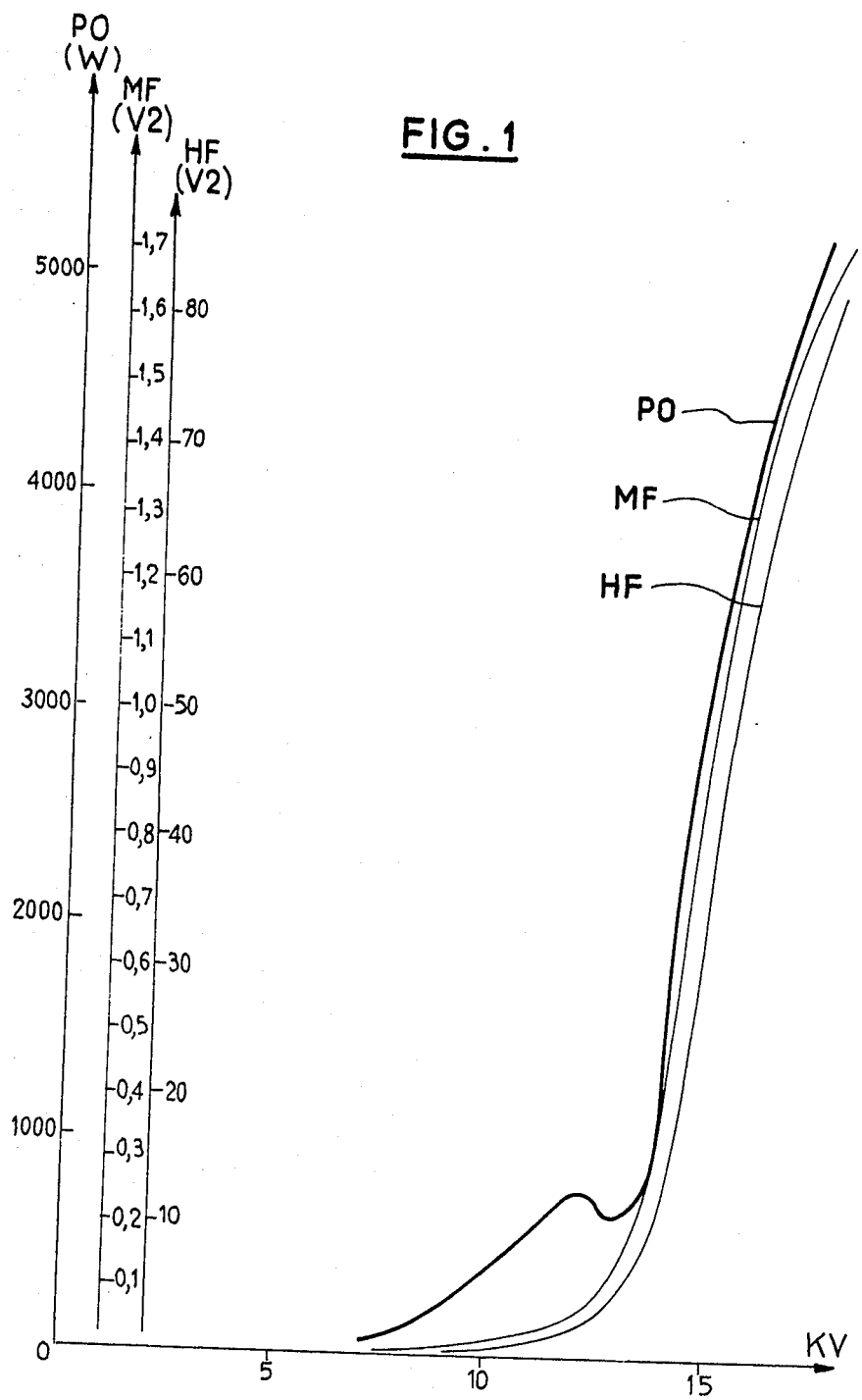
FIG. 1 is a graph showing the curves of the secondary power measured on the transformer supplying power to an ozonizer, of the medium frequency signal and of the high frequency signal measured in this ozonizer as a function of the effective secondary voltage.

As mentioned in the preamble of the present specification, an ozonizer of conventional design comprises a series of pairs of tubular electrodes separated by a dielectric and between which a gas containing oxygen circulates. These pairs of electrodes are supplied with power by the secondary winding of a step-up transformer whose primary winding is supplied with power by a low tension power supply having an industrial frequency (50 or 60 Hz) through a control device which may, for example, be formed by two thyristors mounted in inverted relation and permitting a regulation of the power within a range of between 5 and 100% of the maximum power. The secondary winding of the transformer delivers a high tension current, the peak voltage of which may be of the order of 33 kV.

In such an ozonizer, the electric discharge is constituted by a sum of micro-discharges which issue from fixed regions of the dielectric, and oscillating with damping at a mean frequency of the order of 50 kHz. These discharges, which are termed channels or microchannels depending on their relative amplitude, create in the plasma that they produce oscillations at a high frequency so that:

$$\omega = \sqrt{\frac{n_1 q}{m \epsilon_0}}$$

in which $n_1 = p/q$ is the number of charges per unit volume, p being the total density of free charges, q being the charge and m the mass of the charges, and $\epsilon_0$ being the dielectric constant.

This formula shows that the oscillations, the readings of which, effected on the HF components, show frequencies which vary from 1 to 20 MHz, are the image of the ionic density. Thus, in idustrial ozonizers, ionic densities of $\alpha = 1.424 \times 10^{-4}$ have often been measured.

Now, as shown in FIG. 1, the MF curve of the medium frequency signal and the HF curve of the high frequency signal are, to within scale factors, colinear with the PO curve of the ozonization power, that is to say the power measured at the secondary winding of the transformer supplying power to the ozonizer, in the case of an ozonizer supplied through thyristors connected as triacs. Moreover, trials have shown that the production of ozone or the concentration of ozone in the air are proportional to the ozonization power.

The device according to the invention employs this characteristic of colinearity by permitting the conversion of the measured magnitude of the medium or high frequency signal delivered by the electric discharge in the ozonizer for the purpose of producing a telemeasuring electric signal within the standard ranges of current of from 0 to 20 or from 4 to 20 mA, this signal being the image of the ozonization power, of the production of ozone, or of the concentration of ozone in the air.

Reference will now be made more particularly to FIG. 2 which represents such a device applied to the case of the measurement of the high frequency component produced by the ozonizer. This device comprises a sensor 1 disposed in the vicinity of the ozonizer and which may be formed by a high tension dividing bridge or by a few coils forming an antenna, which may or may not be mounted on a ferrite element, and associated with a current whose curve allows the passage of frequencies of from 1 to 20 MHz with no appreciable amplitude distorsion.

Connected to the output of the sensor 1 are two inverter amplifiers 2 and 3 at the output of which appears the signal 4. This signal is filtered in a high-pass filter 5 which allows the passage of frequencies higher than 1 MHz. At the output of the high-pass filter 5 there is connected an integrator circuit or diode pump 6 comprising a diode 7 connected in series with a resistor 8, a capacitor 9 connected between the output of the resistor 8 and the earth, and a resistor 10 connected in parallel with the capacitor 9.

Connected behind the integrator circuit are a tuner amplifier 11, a multi-function converter 12 converting the input signal into the square of the input signal, while rendering the signal linear depending on the nature, ozonization power or production of ozone, of the physical characteristic of the ozonizer of which this signal must be the image (this multi-function converter may be for example an integrated circuit N° 4 302 of B. BROWN or any like device), and a current generator 13 connected to the output of the converter 12 and producing for example a current of 4/20 mA.

The described circuit is completed by a resistor 14 which symbolizes the charge of the current generator 13, an output terminal 15 from which may be taken a voltage output, and a supply source 16 delivering, from the 50 or 60 Hz voltage of the mains, DC voltages of +15 and −15 volts for the various amplifiers of the circuit.

When the ozonizer, which has not been shown in the drawings, is in operation, the high-frequency pulse trains issuing from the sensor 1 are, after passage through the amplifiers 2 and 3 and the high-pass filter 5, applied to the integrator circuit 6. These pulses charge the capacitor 9 through the diode 7 and the resistor 8. This capacitor is discharged through the resistor 10. The resistors 8 and 10 are different so that the charging and discharging time constants are distinct. Consequently, the capacitor, which stores and makes a sum of the high-frequency pulses, assumes, when balanced, a voltage equal to the algebric sum of that which enters by way of the diode 7 and that which issues by way of the discharge resistor 10. Consequently, when balanced, the voltage at its terminals is the image of the HF signal received. The curve A of FIG. 3 represents the quality of ozone measured in grams as a function of the voltage on the integrator circuit 6. The output signal of the integrator circuit 6, applied to the convertor 12 through the tuner amplifier 11, is rendered linear by this converter 12 which delivers at its output a signal which conforms to the curve B of FIG. 3.

There is consequently provided a measuring device whose output signal is the image of a physical operating characteristic of the ozonizer with which this device is associated, such as, for example, the ozonization power, the production of ozone or the concentration of ozone in the air.

This device may thus be employed in a servo-system in which the output magnitude is a physical or chemical magnitude which is a function of the production of ozone or of the electric power applied to the ozonizer. The signal delivered by the measuring device is then a magnitude which anticipates the function related to the ozonization power. For example, in a servo-system in which the output magnitude is the residual ozone dissolved in the water, this residual ozone is a function of the ozonization power. The measuring device according to the invention enables the ozonization power to be taken as a magnitude anticipating the residual ozone so as to stabilize the servo-system, that is to say to produce an anti-hunting system.

Having now described my invention what I claim as new and desire to secure by Letters Patent is:

1. An apparatus for measuring a physical operating characteristic of an ozonizer which is related to the ozonization power, the production of ozone or the concentration of ozone in the air, said apparatus comprising an ozonizer and a medium or high-frequency sensor placed in the vicinity of the ozonizer for detecting the medium or high-frequency signal emitted by the ozonizer, and an electronic processing ciruit which delivers an electrical signal the voltage of which is proportional to the mean energy content of the medium or high-frequency signal received by the sensor.

2. An apparatus as claimed in claim 1, wherein said sensor is an antenna.

3. An apparatus as claimed in claim 1, wherein said sensor is a high-tension dividing bridge.

4. An apparatus as claimed in claim 1, 2 or 3, wherein said electronic circuit comprises an integrator circuit comprising a capacitor, a diode connected to charge the capacitor, and a resistor connected to discharge the capacitor, said integrator circuit having distinct charging and discharging time constants and being so arranged that, when balanced, the voltage at the terminals of the capacitor is the image of the medium or high-frequency signal received by the sensor.

5. An apparatus as claimed in claim 4, wherein said electronic circuit comprises, between the sensor and the integrator circuit, at least one high-pass filter.

6. An apparatus as claimed in claim 5, wherein the electronic circuit comprises two inverter amplifiers connected between the sensor and the high-pass filter.

7. An apparatus as claimed in claim 4, wherein the electronic circuit comprises a multi-function converter connected downstream of the integrator circuit, said converter raising the signal that it receives from the integrator circuit to the square of this signal and rendering the squared signal linear.

8. An apparatus as claimed in claim 7, comprising a current generator connected to be controlled by the output signal of the converter.

* * * * *